(12) United States Patent
Hong

(10) Patent No.: US 11,377,630 B2
(45) Date of Patent: Jul. 5, 2022

(54) CELL CULTURE KIT

(71) Applicant: Glad I kr Co., Ltd., Suwon-si (KR)

(72) Inventor: Jong-Wook Hong, Suwon-si (KR)

(73) Assignee: Glad I kr Co., Ltd., Suwon-si (KR)

( * ) Notice: Subject to any disclaimer, the term of this patent is extended or adjusted under 35 U.S.C. 154(b) by 495 days.

(21) Appl. No.: 15/989,102

(22) Filed: May 24, 2018

(65) Prior Publication Data

US 2019/0264155 A1   Aug. 29, 2019

(30) Foreign Application Priority Data

Feb. 28, 2018   (KR) .......................... 10-2018-0024330

(51) Int. Cl.
| | | |
|---|---|---|
| *C12M 1/00* | (2006.01) | |
| *C12M 1/12* | (2006.01) | |
| *C12N 5/00* | (2006.01) | |
| *C12M 3/00* | (2006.01) | |

(52) U.S. Cl.
CPC ............ *C12M 25/00* (2013.01); *C12M 23/50* (2013.01); *C12M 23/54* (2013.01); *C12M 25/02* (2013.01); *C12N 5/0062* (2013.01); *C12N 2513/00* (2013.01)

(58) Field of Classification Search
CPC .............. B41C 1/1008; B41C 2210/04; B41C 2210/06; B41C 2210/22; B41C 2210/24; B41C 2210/262; G03F 7/0045; G03F 7/038; Y10S 430/115; Y10S 430/118; Y10S 430/128; C12M 23/50; C12M 23/54; C12M 25/00; C12M 25/02; C12M 25/06; C12N 2513/00; C12N 2533/30; C12N 2535/00; C12N 5/0062; C12N 5/0068; E05F 11/382; E05Y 2900/55; Y10T 74/2158

See application file for complete search history.

(56) References Cited

U.S. PATENT DOCUMENTS

2017/0051241 A1*   2/2017   Obi .................. C12M 25/04

FOREIGN PATENT DOCUMENTS

| JP | 2001-507218 A | 6/2001 |
|---|---|---|
| JP | 2017-085960 A | 5/2017 |
| KR | 10-2011-0091078 A | 8/2011 |
| KR | 10-1390755 B1 | 4/2014 |
| KR | 10-1717814 B1 | 3/2017 |
| KR | 10-2017-0052524 A | 5/2017 |
| WO | 1998/024880 A1 | 6/1998 |
| WO | 2007/114421 A1 | 10/2007 |
| WO | 2012/045368 A1 | 4/2012 |
| WO | 2016/035407 A1 | 3/2016 |

OTHER PUBLICATIONS

John A. Ryan, Ph.D., Corning Incorporated Life Sciences, "Growing More Cells : A Simple Guide to Small Volume Cell Culture Scale-Up" (2008), 16pages.
International Search Report and Written Opinion of the International Searching Authority dated Nov. 27, 2018 for Application No. PCT/KR2018/005044, 13pages.

* cited by examiner

*Primary Examiner* — Lydia Edwards
(74) *Attorney, Agent, or Firm* — Park, Kim & Suh, LLC

(57) ABSTRACT

A cell culture kit is provided. The cell culture kit allows a cultured cell to be easily separated when the cell is cultured and separates a cell without separate trypsinization for subculture.

14 Claims, 22 Drawing Sheets

CELL CULTURE KIT

CROSS-REFERENCE TO RELATED APPLICATIONS

This application claims priority from Korean Patent Application No. 10-2018-0024330, filed on Feb. 28, 2018, in the Korean Intellectual Property Office, the disclosure of which is incorporated herein by reference in its entirety.

BACKGROUND OF THE INVENTION

Field of the Invention

The present invention relates to a cell culture kit, and more particularly, to a cell culture kit for easily separating and observing a cultured cell in the case of cell culture and also separating the cell without separate trypsinization of the engrafted cell even in the case of subculture.

Description of the Related Art

Cell or tissue culture technologies are very basic and important in biology research including molecular biology and have been applied to various fields such as cancer diagnosis research, research for development of novel medicines as well as cancer treatment materials, gene therapy research, stem cell differentiation research, and characteristics material generating research.

With regard to cells cultured using various methods for the purpose of the aforementioned researches, live cell research has been conducted to functionally or morphologically study the cell in a live state or a cell or tissue fixative is selected and fixed to prevent cell metamorphosis, immunocytology staining or immunofluorescent staining is completely performed on the cell using a series of processes and the cell is sealed and, then, the cell is observed using a microscope for serving the purpose of experiment, such as a light microscope, a fluorescent microscope, and a confocal laser microscope, thereby ensuring reliability in terms of quantification of an experimental result and experiment reproducibility.

A conventional analysis method via cell culture is described below.

First, the analysis method includes putting a sterilized cover glass in a circular cell or tissue culture container, culturing a cell on the cover glass to form layers of engrafted cells, separating the cover glass from a culture dish, attaching the resultant to a cover glass for biopsy and, then, observing and analyzing the resultant using a microscope for serving the purpose of research.

However, the aforementioned method has several problems. First, an engraftment rate of a cell strain that is adapted to be engrafted and grown on a plastic cell culture surface is changed above a cover glass formed of glass to change cell properties. Second, a cell culture environment is changed during a process of inserting an external cover glass into the cell culture container and, in more serious cases, internal contamination may occur during cell culture. Third, there is risk of breaking a cover glass on which a cell is engrafted during a series of processes including cell culture to microscope observation due to the properties whereby glass is easily broken. Fourth, an experimental group and a control group are obtained by culturing cells on cover glasses on different cell culture containers and, thus, the possibility that an error arises in observation and analysis is frequently increased.

In particular, the conventional analysis method via cell culture frequently requires subculture. That is, when a cell or a tissue is cultured on a culture dish, the cell or the tissue is attached to the dish and continuously proliferates as a single layer and, thus, occupies the entire culture dish and stops proliferating over time due to insufficient space. In this case, to allow a cell or a tissue to continuously proliferate, subculture of taking a partial piece of the corresponding cell and moving the taken partial piece to another culture dish needs to be performed. Subculture requires trypsinization to separate a cell or a tissue from a conventional culture dish.

However, in this case, it is difficult to accurately separate the cultured cell or tissue. In addition, there is a problem in that the cell or the tissue is metamorphosed during a trypsinization process to separate the cultured cell or tissue.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above.

The present invention provides a cell culture kit for easily separating and observing a cultured cell or tissue.

The present invention provides a cell culture kit for preventing change in an engraftment rate of a cell to prevent change in a cell culture environment without injection of an external cover glass into a cell culture container.

The present invention provides a cell culture kit for enhancing user convenience and preventing a cell from being damaged without trypsinization that was a required process for subculture of a grown cell.

The present invention provides a cell culture kit that 2-dimenisonally grows a cell or a tissue and, simultaneously, grows a 3D cell assembly to observe and examine the cell assembly.

According to an aspect of the present invention, a cell culture kit includes an external container configured with an open top to provide an accommodation space therein, a cell culture film formed by detachably stacking at least one piece inside the external container, and a cover portion coupled to the open top of the external container.

The cell culture film may be formed of a polystyrene film or a silicone polymer.

The cell culture film may have a thickness of 0.1 to 0.2 mm.

The cell culture film may have a refractive index corresponding to 1.4 to 1.6.

The cell culture film may have dotted lines formed thereon.

The cell culture kit may further include a handle portion formed by bending upward at least a portion of an edge of the cell culture film.

The cell culture kit may further include a plurality of culture holes formed in the cell culture film.

A culture hole of the cell culture film may not overlap with a culture hole of an underlying cell culture film.

An upper surface of a base of the external container or an upper surface of the underlying cell culture film may be exposed through the culture hole of the cell culture film.

The cell culture film may include one or more cell culture grooves protruding downward to culture a cell assembly therein, and an accommodation groove for accommodation of the cell culture grooves therein may be formed in the base of the external container to correspond to the cell culture grooves.

The cell culture film with the cell culture groove therein may be positioned at a lowermost layer and at least one cell culture film with a plurality of culture holes formed therein is positioned at an upper portion.

At least one of the plurality of culture holes may be disposed to be connected to the cell culture grooves, and remaining culture holes of the cell culture film may not overlap with a culture hole of a cell culture film at a lower layer.

The cell culture kit may further include a side wall bent upward from an edge of the cell culture film.

The side wall of the cell culture film may be formed to be inclined outward at a predetermined angle based on a vertical line.

The cell culture film may include a plurality of culture holes formed therein.

A culture hole of the cell culture film may not overlap with a culture hole of a cell culture film at a lower layer.

The cell culture kit may further include a handle disposed at an upper end portion of the side wall of the cell culture film.

A height of an upper end portion of the side wall of the cell culture film may be higher than a height of an upper end portion of a side wall of the external container.

When the upper end portion of the side wall of the cell culture film is folded outward, an upper end portion of the side wall of the external container may be covered by the folded upper end portion of the cell culture film.

The cover portion may include an external cover and an internal cover that is detachably stacked inside the external cover to correspond to the number of the cell culture films.

The internal cover may further include a handle.

BRIEF DESCRIPTION OF THE DRAWING FIGURES

The above and/or other aspects of the present invention will be more apparent by describing certain exemplary embodiments of the present invention with reference to the accompanying drawings, in which.

DETAILED DESCRIPTION OF THE EXEMPLARY EMBODIMENTS

Figure 1:
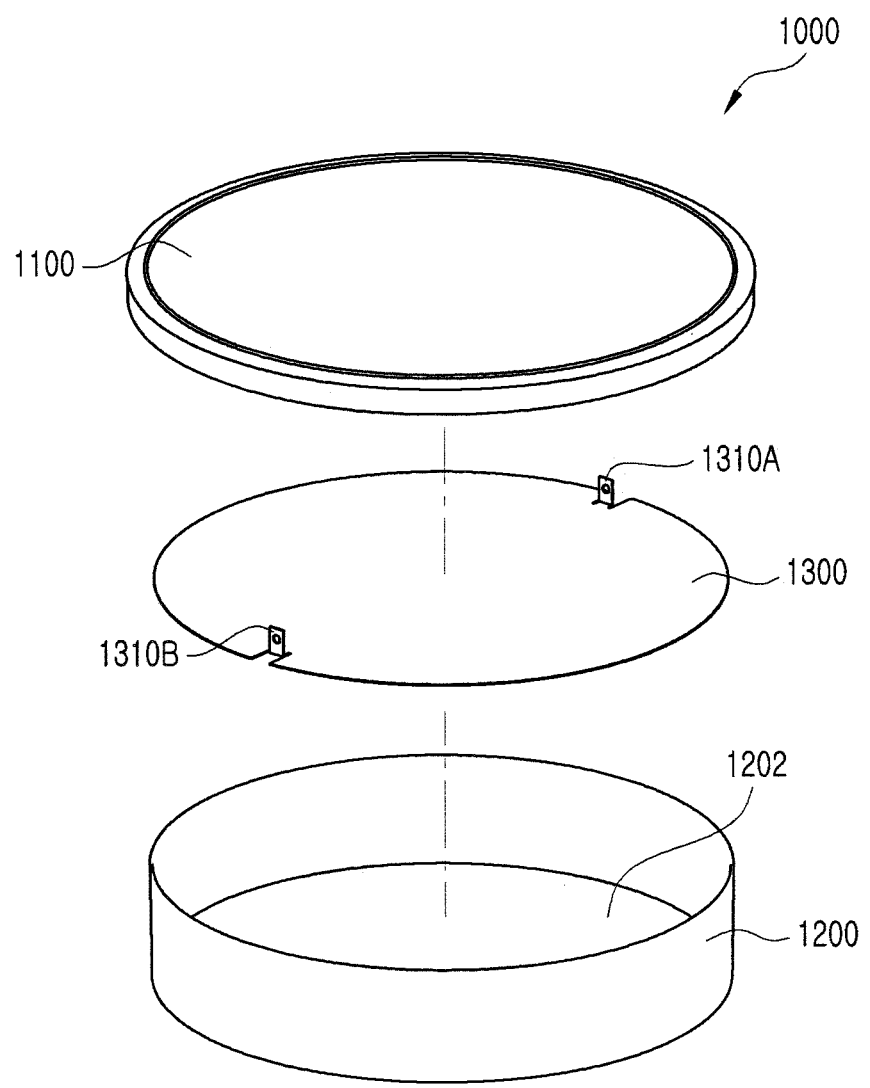
FIG. 1 is an exploded perspective view of a cell culture kit according to an embodiment of the present invention.

Reference will now be made in detail to the exemplary embodiments of the present invention with reference to the accompanying drawings. Unless otherwise defined, all terms used in this specification have the same meaning as commonly understood by one of ordinary skill in the art to which this invention belongs and, when a term used in this specification is different from general meaning, the term is understood as definition used in this specification. A configuration or control method of an apparatus to be described below is intended merely to embodiments of the present invention and should not be construed as limited to the exemplary embodiments set forth herein and, throughout this specification, the same reference numeral denote the same element.

Figure 2:
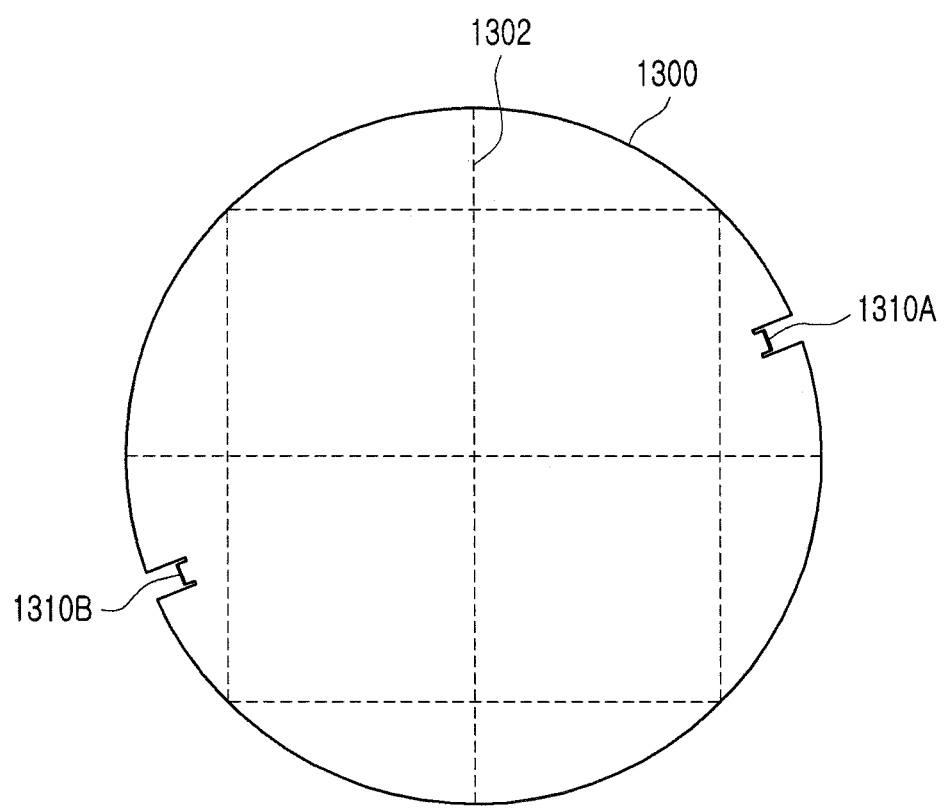
FIG. 2 is a plan view of a cell culture film illustrated in FIG. 1.

FIG. 1 is an exploded perspective view of a cell culture kit 1000 according to an embodiment of the present invention. FIG. 2 is a plan view of a cell culture film 1300 illustrated in FIG. 1.

Referring to FIGS. 1 and 2, the cell culture kit 1000 may include an external container 1200 configured with an open top to provide an accommodation space therein, the cell culture film 1300 formed by detachably stacking at least one piece inside the external container 1200, and a cover portion 1100 coupled to the open top of the external container 1200.

The cell culture kit 1000 according to the present invention may include the cell culture film 1300 that is separately installed in the external container 1200 to culture a cell or a tissue. In this case, the cell or the tissue is cultured on an upper surface of the cell culture film 1300 and, then, the cell culture film 1300 on which the cell or the tissue is cultured is separated from the external container 1200 without separately separating the cultured cell or tissue and, thus, a procedure of separating the cell or the tissue from a film may be omitted. In addition, the cell culture film 1300 may be used in a microscope for biopsy, or the like without change instead of a cover glass to prevent metamorphosis of a tissue or a cell during separation of the cell or the tissue and, furthermore, a separation procedure of the cell or the tissue may be omitted and, thus, the tissue or the cell may be rapidly and simply observed. Hereinafter, a configuration of the cell culture kit 1000 is described in more detail.

As illustrated in FIGS. 1 and 2, the external container 1200 may accommodate the aforementioned cell culture film 1300 therein to provide a space for culturing a cell or a tissue.

In this case, as illustrated, the external container 1200 may be configured with an open top to accommodate the cell culture film 1300 therein. The external container 1200 may have a circular section but is not limited thereto and, as necessary, may be changed appropriately.

A material of the external container 1200 may be appropriately selected and, for example, the external container 1200 may be formed of synthetic resin or the like using a method such as blowing or injection.

The cover portion 1100 may be coupled to the open top of the external container 1200.

The cover portion 1100 may be coupled to the open top of the external container 1200 and, thus, when a cell or a tissue is cultured using the cell culture film 1300, microorganisms, foreign substances, or the like may be prevented from internally penetrating.

In this case, the cover portion 1100 may have a shape corresponding to a shape of the section of the external container 1200 to be coupled to the open top of the external container 1200. The cover portion 1100 may be formed of synthetic resin or the like using a method such as blowing or injection, like the external container 1200.

The cell culture film 1300 may be included inside the external container 1200. According to the present embodiment, the case in which the number of the cell culture film 1300 is one is described, but the cell culture film 1300 may be provided in two or more, i.e., in plural, to configure an assembly. An embodiment in which the cell culture film 1300 is provided in plural, to configure an assembly is described below in detail.

The cell culture film 1300 may be formed to correspond to a shape of the section of the external container 1200 and may be positioned inside the external container 1200. As illustrated in FIGS. 1 and 2, when the section of the external container 1200 has a circular shape, the cell culture film 1300 may also have a circular shape corresponding to the section of the external container 1200.

The cell culture film 1300 may be detachably positioned inside the external container 1200. For example, the cell culture film 1300 may be heated to a predetermined temperature to be adhered to a base 1202 of the external container 1200 or the cell culture film 1300 and the base 1202 may be adhered using an adhesive formed of a material that does not affect growth of a cell or a tissue, such as resin or polymer resin of a silicone material. Here, "adhesion" may be defined as a state in which the cell culture film 1300 is attached to an internal side of the external container 1200 but is easily separated from the external container 1200 without contamination of the cell culture film 1300 or the external container 1200.

At least a portion of an edge of the cell culture film 1300 may be bent upward to form handle portions 1310A and 1310B. To separate the cell culture film 1300 from the base 1202 inside the external container 1200, a separate device such as a pair of tweezers may be used. However, it may not be easy to separate the very thin cell culture film 1300 using the separation device and, in this regard, the cell or the tissue of the cell culture film 1300 may be metamorphosed during the separation procedure.

Accordingly, the cell culture film 1300 according to the present embodiment may include the pair of handle portions 1310A and 1310B that are formed along the edge of the cell culture film 1300 to easily separate the cell culture film 1300 from the external container 1200. In this case, to form the handle portions 1310A and 1310B, a separate member is not attached to the cell culture film 1300 and, instead, a portion of the edge of the cell culture film 1300 may function as a handle.

In detail, the pair of handle portions 1310A and 1310B may be symmetrically arranged about a central portion of the cell culture film 1300. In this case, a portion of an edge of the cell culture film 1300 may be cut and bent upward to form the handle portions 1310A and 1310B.

Accordingly, an operator may culture a cell or a tissue on an upper surface of the cell culture film 1300 and, then, pull the handle portions 1310A and 1310B from the external container 1200 to easily separate the cell culture film 1300 from the external container 1200.

However, a cell or a tissue is cultured on the upper surface of the cell culture film 1300 disposed inside the external container 1200 and the cell culture film 1300 is separated and, then, the tissue or the cell is separated from the cell culture film 1300 and is moved to a cover glass for biopsy or the like to observe the cultured tissue or cell and, in this case, the cultured tissue or cell may be metamorphosed.

Accordingly, to overcome the aforementioned problem, when the cell culture film 1300 on which a cell or a tissue is cultured is separated from the external container 1200, the cell culture film 1300 may be immediately injected into a microscope for observation, such as a fluorescent microscope, to function as a cover glass for observation.

To this end, the cell culture film 1300 may have a thickness of about 0.1 mm to 0.2 mm and may be manufactured with a refractive index corresponding to about 1.4 to 1.6 to have a similar refractive index to a cover glass.

The cell culture film 1300 may be formed of a transparent biocompatible material. For example, the cell culture films 5300A to 5300G may be formed of polydimethylsiloxane (PDMS), poly(methylmethacrylate) (PMMA), a polystyrene film, or a silicone polymer.

Accordingly, when the cell culture film 1300 on which a cell or a tissue is cultured is separated, the separated cell culture film 1300 may be injected into a microscope for examination to immediately perform examination and to conveniently perform examination without moving the cultured cell or tissue to a separate cover glass for examination. Properties such as the thickness, material, and transmissive properties of the cell culture film 1300 may be applied to all cell culture films of the cell culture kit according to exemplary embodiments to be described below.

When the cell culture film 1300 is provided in plural, a cultured cell or tissue may need to be segmented for various types of experiments or observations. In this case, to segment the cell culture film 1300, dotted lines 1302 may be formed on the cell culture film 1300, as illustrated in FIG. 2.

Although FIG. 2 illustrates the case in which the dotted lines 1302 are formed in parallel to each other to divide a central portion of the cell culture film 1300 into four sections, the dotted lines 1302 may be formed in various forms as necessary.

Accordingly, when a cell or a tissue is cultured on an upper surface of the cell culture film 1300 and, then, the cell culture film 1300 is torn along the dotted line 1302, the cell culture film 1300 may be segmented into a plurality of pieces to repeatedly perform observation or experiment for an appropriate purpose.

Figure 3:
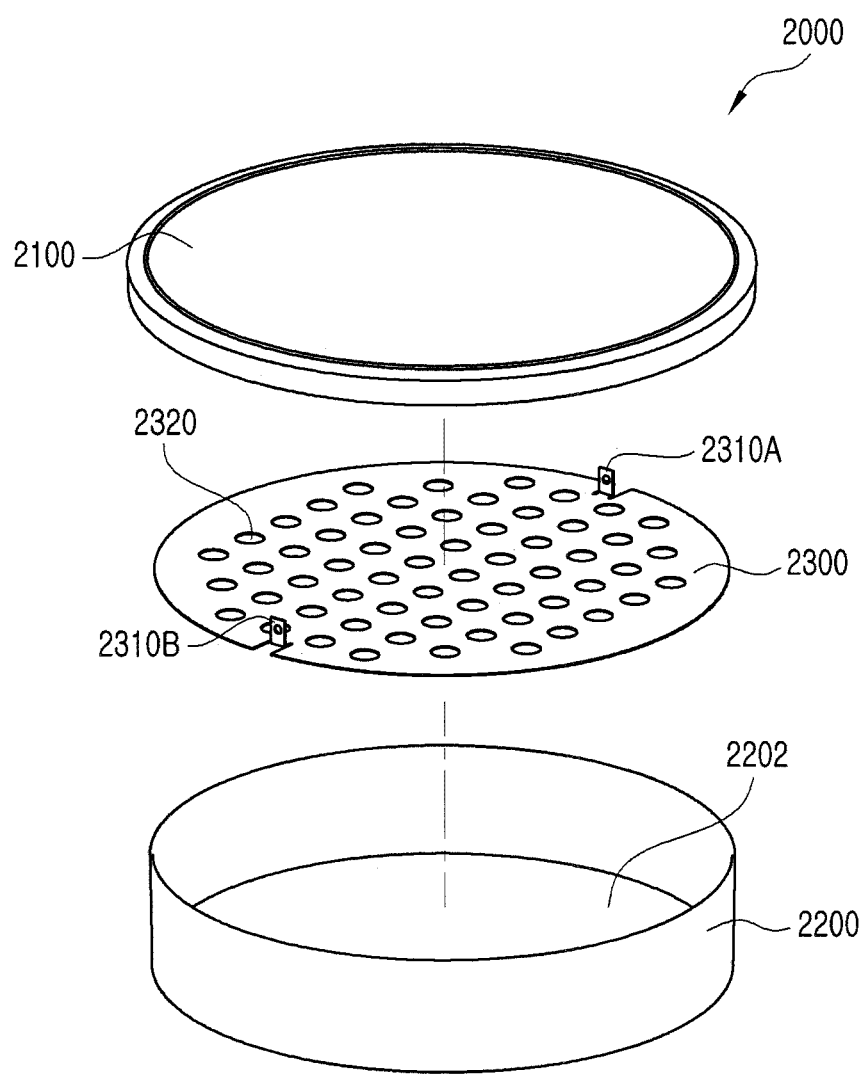
FIG. 3 is an exploded perspective view of a cell culture kit according to another embodiment of the present invention.
Figure 4:
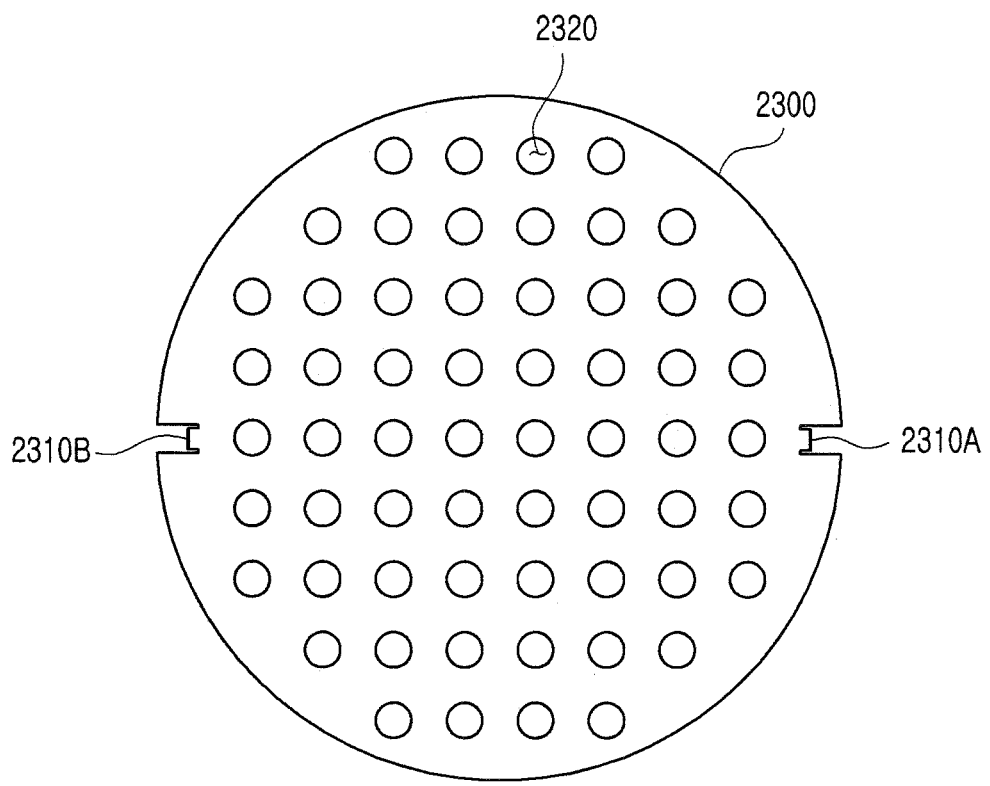
FIG. 4 is a plan view of a cell culture film illustrated in FIG. 3.

FIG. 3 is an exploded perspective view of a cell culture kit 2000 according to another embodiment of the present invention. FIG. 4 is a plan view of a cell culture film 2300 illustrated in FIG. 3.

Referring to FIGS. 3 and 4, the cell culture kit 2000 may include an external container 2200 that is configured with an open top to provide an accommodation space therein, the cell culture film 2300 formed by detachably stacking at least one piece inside the external container 2200, and a cover portion 2100 coupled to the open top of the external container 2200.

In this case, a plurality of culture holes 2320 may be formed in the cell culture film 2300 according to the present embodiment.

That is, the cell culture film 2300 may include the plural culture holes 2320 formed therethrough, as illustrated in FIGS. 3 and 4. Accordingly, when the cell culture film 2300 is positioned on a base 2202 inside the external container 2200, an upper surface of the base 2202 inside the external container 2200 may be exposed through the culture holes 2320.

In the case of the prior art, when subculture is performed on a cell or a tissue, trypsinization is performed on a cell or tissue cultured on a culture dish and the cell or the tissue are separated. However, trypsinization is a very sensitive process and, in this regard, it is difficult to accurately separate the cultured cell or tissue. In addition, there is a problem in that a cell or a tissue is metamorphosed during trypsinization to separate the cultured cell or tissue.

However, in the case of the cell culture kit 2000 according to the present embodiment, when subculture is performed on a cell or a tissue, it is advantageous that trypsinization of a cell or a tissue as in the aforementioned prior art is omitted and the cell or the tissue is easily separated.

FIGS. 5A to 5D are schematic diagrams showing a subculture procedure using the cell culture kit 2000 according to the present embodiment. The subculture procedure of a cell or a tissue is described below with reference to FIGS. 5A to 5D.

Figure 5A:
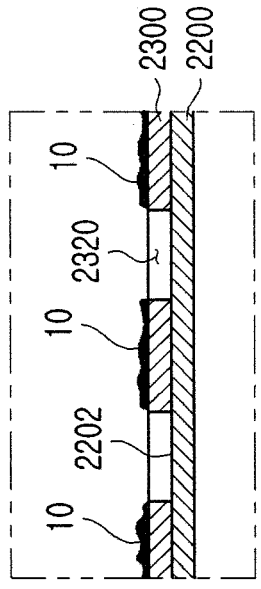
FIGS. 5A to 5D are schematic diagrams showing a subculture procedure using the cell culture film illustrated n FIG. 4.

First, as illustrated in FIG. 5A, the cell culture film 2300 may be positioned on the base 2202 inside the external container 2200.

Figure 5B:
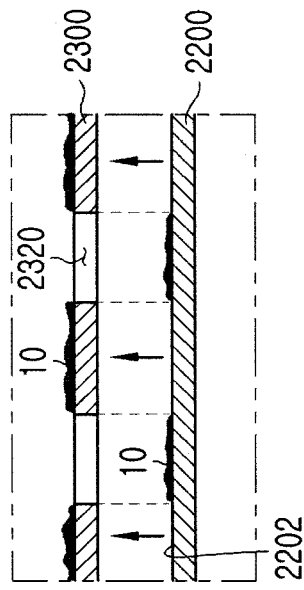

Then, as illustrated in FIG. 5B, a cell or tissue 10 may be cultured on an upper surface of the cell culture film 2300.

Figure 5C:
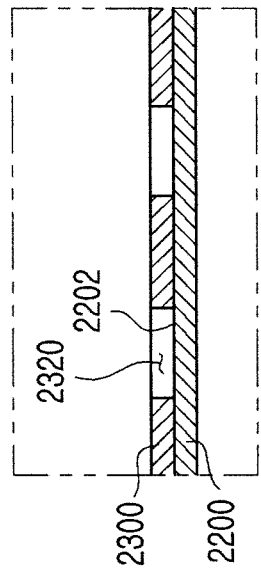

In this case, the cell or tissue 10 may be cultured to cover the upper surface of the cell culture film 2300 and, then, as illustrated in FIG. 5C, may also be cultured on an upper surface of the base 2202 of the external container 2200, which is exposed through the culture holes 2320.

Figure 5D:
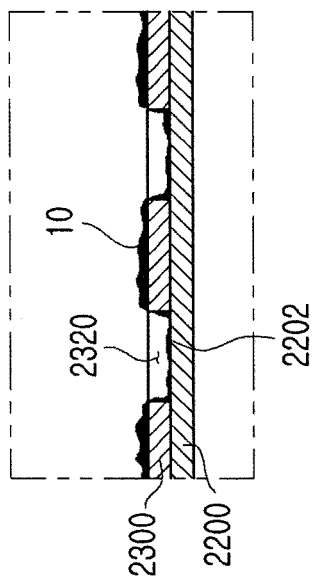

In this case, when an operator pulls handle portions 2310A and 2310B (refer to FIG. 3) of the cell culture film 2300 to separate the cell culture film 2300 from the external container 2200 as shown in FIG. 5D, the cultured cell or tissue may remain on the upper surface of the base 2202 inside the external container 2200 as well as the upper surface of the cell culture film 2300.

Accordingly, a cell or a tissue may be continuously cultured on the base 2202 of the external container 2200 and, thus, separate trypsinization for separating the cell or the tissue for subculture may not be required unlike in the prior art.

In this case, the cell or the tissue may be cultured on the base 2202 inside the external container 2200 and, thus, the external container 2200 according to the present embodiment may be formed of the same material as the cell culture film 2300. That is, the external container 2200 may be formed of a biocompatible material such as polydimethylsiloxane (PDMS), poly(methylmethacrylate) (PMMA), a polystyrene film, or a silicone polymer.

Figure 6:
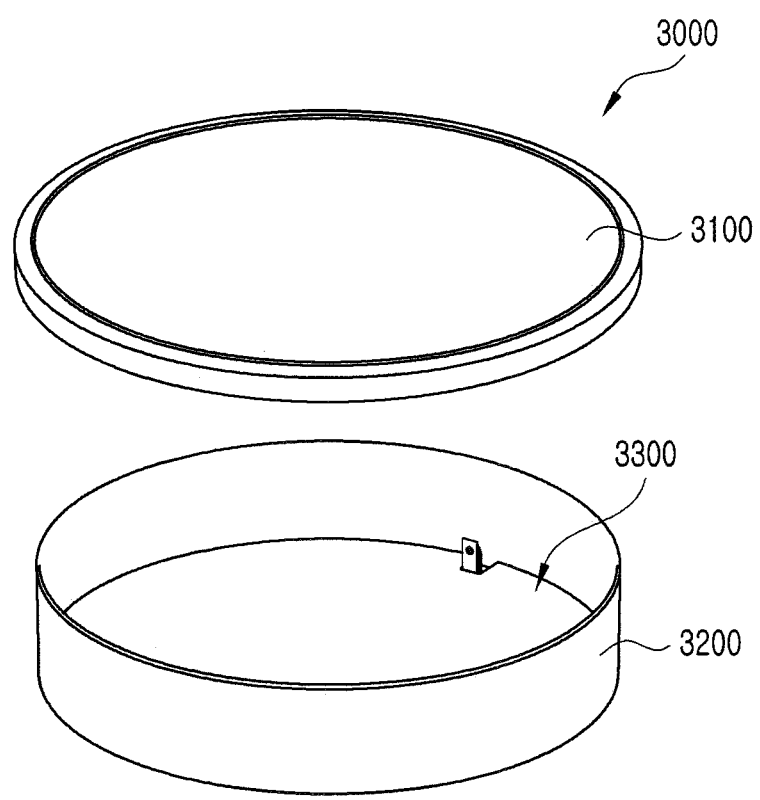
FIG. 6 is a perspective view of a cell culture kit according to an embodiment of the present invention.
Figure 7:
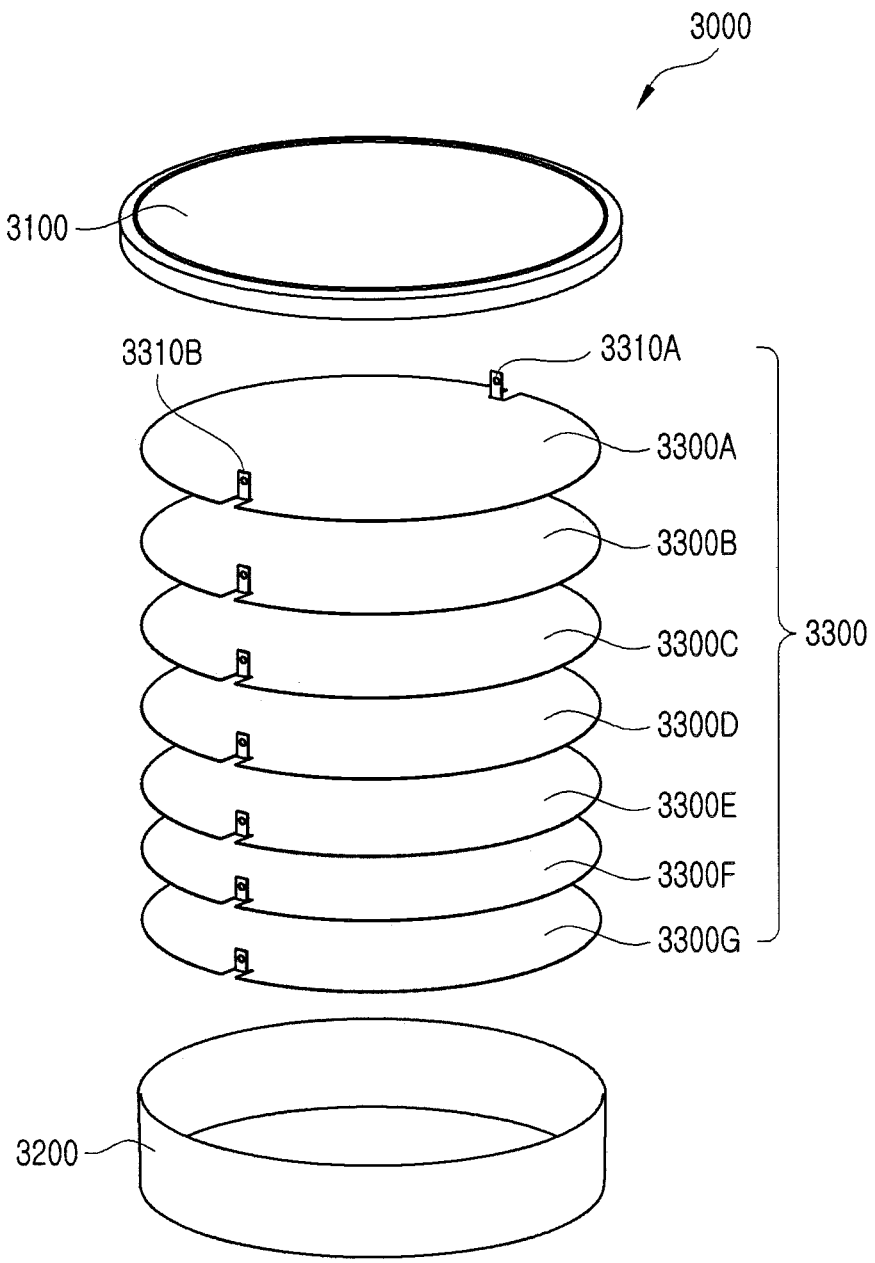
FIG. 7 is an exploded perspective view of a cell culture kit illustrated in FIG. 6.

FIG. 6 is a perspective view of a cell culture kit 3000 according to an embodiment of the present invention. FIG. 7 is an exploded perspective view of the cell culture kit 3000.

Referring to FIGS. 6 and 7, the cell culture kit 3000 may include an external container 3200 that is configured with an open top to provide an accommodation space therein, cell culture films 3300A to 3300G formed by detachably stacking at least one piece inside the external container 3200, and a cover portion 3100 coupled to the open top of the external container 3200.

In this case, the cell culture films 3300A to 3300G may be configured in plural, to configure a cell culture film assembly 3300. That is, as shown in FIG. 7, the cell culture film assembly 3300 may be formed by stacking the plural separate cell culture films 3300A to 3300G. Handle portions 3310A and 3310B formed in each of the separate cell culture films 3300A to 3300G are similar to the aforementioned embodiment and, thus, a repeated description thereof is not omitted herein.

When the cell culture films 3300A to 3300G are configured in plural, if a cell or a tissue is cultured using the cell culture kit 3000 according to the present embodiment, the cell culture kit 3000 may be advantageously and repeatedly used rather than being discarded after cell culture is completed once.

That is, after a cell or a tissue is cultured on the cell culture film 3300A positioned at a first layer (uppermost layer), the cell culture film 3300A may be separated and a cell or a tissue may be newly cultured on the cell culture film 3300B positioned at a second layer that is a lower layer of the first layer. Accordingly, the cell culture kit 3000 may be repeatedly used by as much as the number of the cell culture films 3300A to 3300G and, thus, economic efficiency may be enhanced compared with a cell culture film that is used once and then discarded and a cell is more conveniently and easily examined and observed.

In this case, when the cell culture films 3300A to 3300G are configured in plural, the plural cell culture films 3300A to 3300G may be detachably stacked. For example, the plural cell culture films 3300A to 3300G may be heated to a predetermined temperature to be adhered to each other or may be adhered to each other using an adhesive formed of a material that does not affect growth of a cell or a tissue, such as resin or polymer resin of a silicone material.

Here, "adhesion" may be defined as a state in which the plural cell culture films 3300A to 3300G are attached to each other but are easily separated from each other without contamination of another cell culture film.

Figure 8:
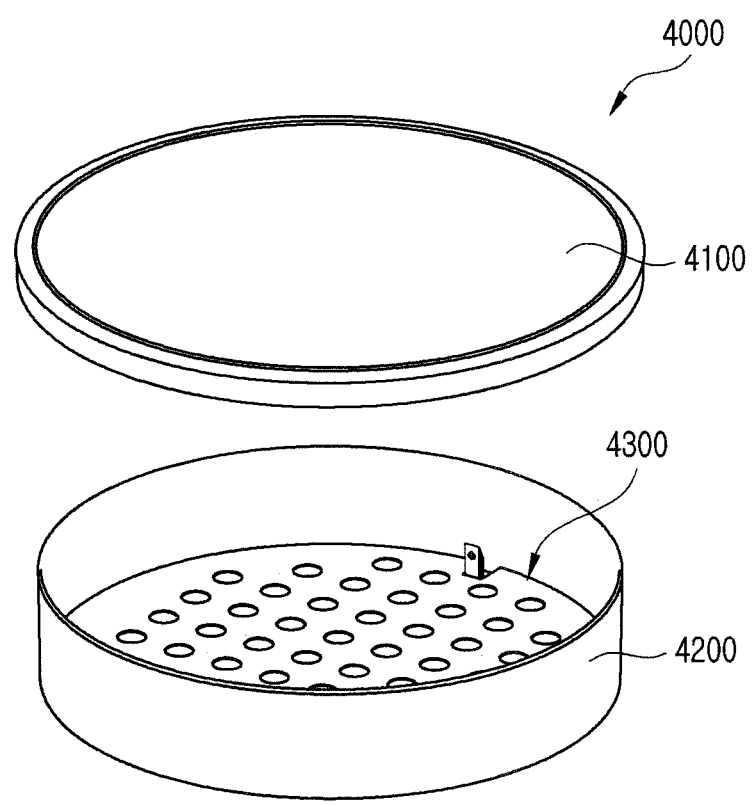
FIG. 8 is a perspective view of a cell culture kit according to another embodiment of the present invention.
Figure 9:
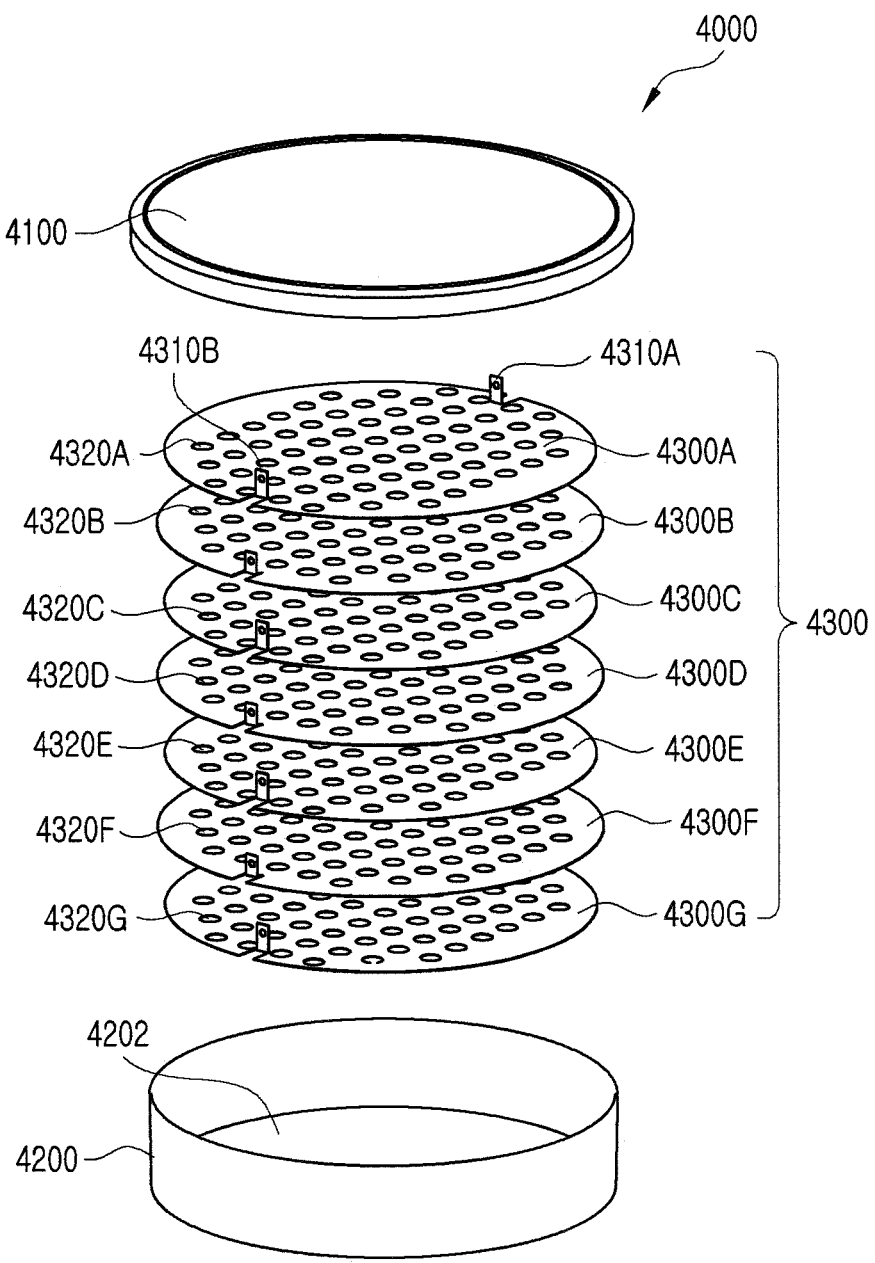
FIG. 9 is an exploded perspective view of the cell culture kit illustrated in FIG. 8.

FIG. 8 is a perspective view of a cell culture kit 4000 according to another embodiment of the present invention. FIG. 9 is an exploded perspective view of the cell culture kit 4000.

Referring to FIGS. 8 and 9, the cell culture kit 4000 may include an external container 4200 that is configured with an open top to provide an accommodation space therein, cell culture films 4300A to 4300G formed by detachably stacking at least one piece inside the external container 4200, and a cover portion 4100 coupled to the open top of the external container 4200.

In this case, the cell culture films 4300A to 4300G may be configured in plural, to configure a cell culture film assembly 4300 and the plural cell culture films 4300A to 4300G may include a plurality of culture holes 4320A to 4320G, respectively.

Figure 10:
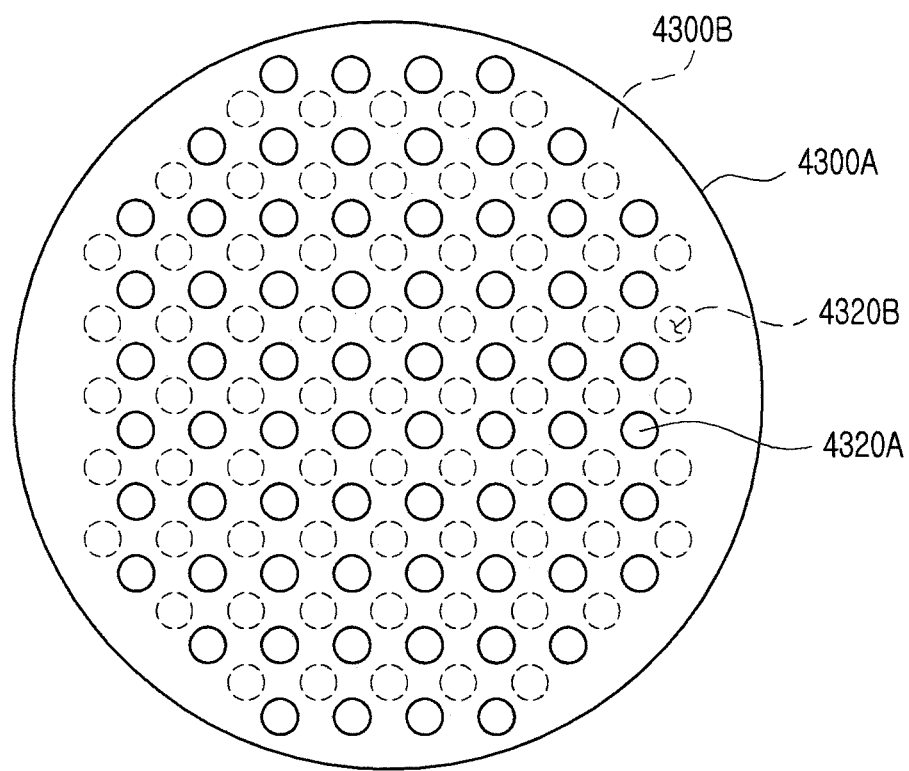
FIG. 10 is a plan view of the cell culture film illustrated in FIG. 9.

FIG. 10 is a plan view of the cell culture film assembly 4300.

Referring to FIG. 10, the culture holes 4320A to 4320G of the cell culture films 4300A to 4300G may be configured in such a way that culture holes of a cell culture film do not overlap with culture holes of a lower cell culture film.

That is, as illustrated in FIG. 10, the culture holes 4320A of the cell culture film 4300A at a first layer may be formed not to overlap with the culture holes 4320B of the cell culture film 4300B at a second layer positioned lower than the first layer.

Accordingly, the culture holes 4320A to 4320G of the cell culture films 4300A to 4300G may be configured to expose an upper surface of a cell culture film at an immediately lower layer through the culture holes 4320A to 4320G of the cell culture films 4300A to 4300G.

That is, as described above with reference to FIG. 3, when the number of the cell culture film 2300 including the culture holes 2320 formed therein is one, the upper surface of the base 2202 of the external container 2200 is exposed through the culture holes 2320 of the cell culture film 2300 and, as illustrated in FIG. 9, when the plural separate cell culture films 4300A to 4300G are used, an upper surface of a cell culture film at an immediately lower layer may be through the culture holes 4320A to 4320G of the cell culture films 4300A to 4300G. When the plural separate cell culture films 4300A to 4300G are used, an upper surface of a base 4202 of the external container 4200 may also be exposed through the culture holes 4320G of the cell culture film 4300G at a lowermost layer. As a result, the upper surfaces of the bases 2202 and 4202 of the external containers 2200 and 4200 or an upper surface of a cell culture film at a lower layer may be exposed through the culture holes 2320 and 4320A to 4320G of the cell culture films 2300 and 4300A to 4300G.

In the case of the cell culture kit 4000 according to the present embodiment, trypsinization for separation of a cultured cell or tissue for subculture may be omitted like in the embodiments shown in FIGS. 3 to 5.

FIGS. 11A to 11D are schematic diagrams showing a subculture process using the cell culture kit 4000 according to the present embodiment. For convenience of description, FIGS. 11A to 11D illustrate only the cell culture film 4300A at the first layer and the cell culture film 4300B at the second layer that is a lower layer of the first layer among the plural cell culture films 4300A to 4300G. With reference to FIGS. 11A to 11D, the subculture process of a cell or a tissue is described below.

Figure 11B:
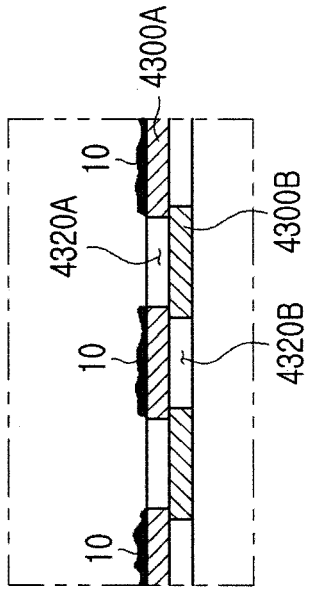
FIGS. 11A to 11D are schematic diagrams showing a subculture process using the cell culture kit illustrated in FIG. 9.
Figure 11D:
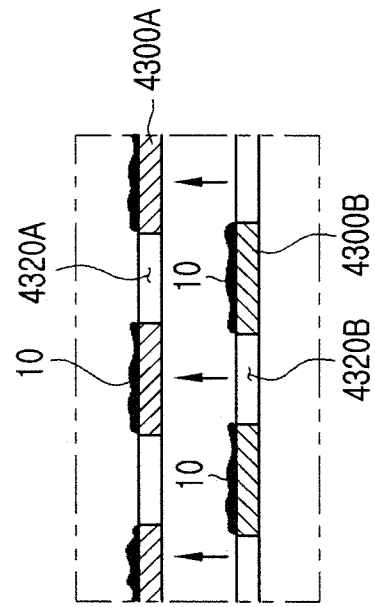
Figure 11A:
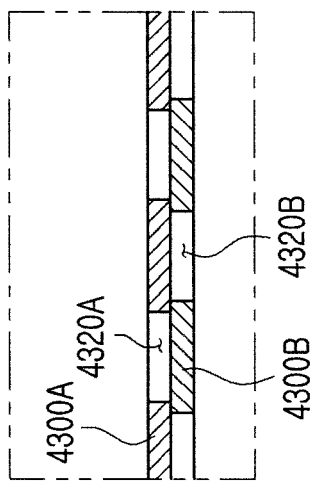

First, as shown in FIG. 11A, the cell culture film 4300A at the first layer may be disposed on the cell culture film 4300B at the second layer. In this case, the culture holes 4320A of the cell culture film 4300A at the first layer may be formed not to overlap with the culture holes 4320B of the cell culture film 4300B at the second layer positioned lower than the first layer. Accordingly, an upper surface of the cell culture film 4300B at an immediately lower layer may be exposed through the culture holes 4320A of the cell culture film 4300A at the first layer.

Then, as illustrated in FIG. 11B, the cell or tissue 10 may be cultured on the upper surface of the cell culture film 4300A at the first layer.

Figure 11C:
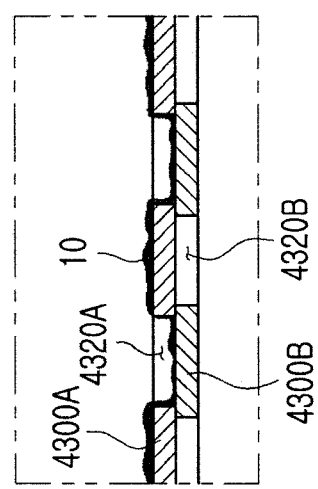

In this case, the cell or tissue 10 may be cultured to cover the upper surface of the cell culture film 4300A at the first layer and, then, as illustrated in FIG. 11C, may also be cultured on an upper surface of the cell culture film 4300B at the second layer, which is exposed through the culture holes 4320A.

In this case, when an operator pulls handle portions 4310A and 4310B of the cell culture film 4300A at the first layer to separate the cell culture film 4300A at the first layer from the cell culture film 4300B at the second layer as shown in FIG. 11D, the cultured cell or tissue may remain on a portion of the upper surface of the cell culture film 4300B at the second layer as well as the upper surface of the first layer.

Accordingly, a cell or a tissue may be continuously cultured on the upper surface of the cell culture film 4300B at the second layer and, thus, separate trypsinization for separating the cell or the tissue for subculture may not be required unlike in the prior art.

The subculture process may be repeatedly performed. That is, although not illustrated in FIGS. 11A to 11D, the cell culture film 4300C at a third layer may be positioned below the cell culture film 4300B at the second layer. Accordingly, the aforementioned process of FIGS. 11A to 11D may be repeatedly performed to repeatedly perform the subculture process in which trypsinization is omitted.

Figure 12:
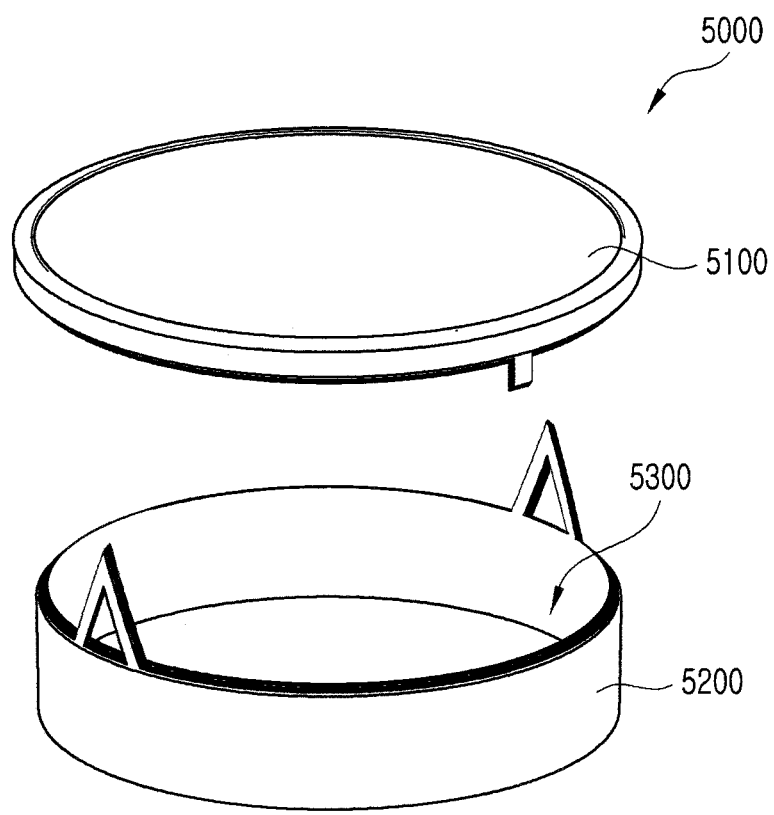
FIG. 12 is a perspective view of a cell culture kit according to another embodiment of the present invention.
Figure 13:
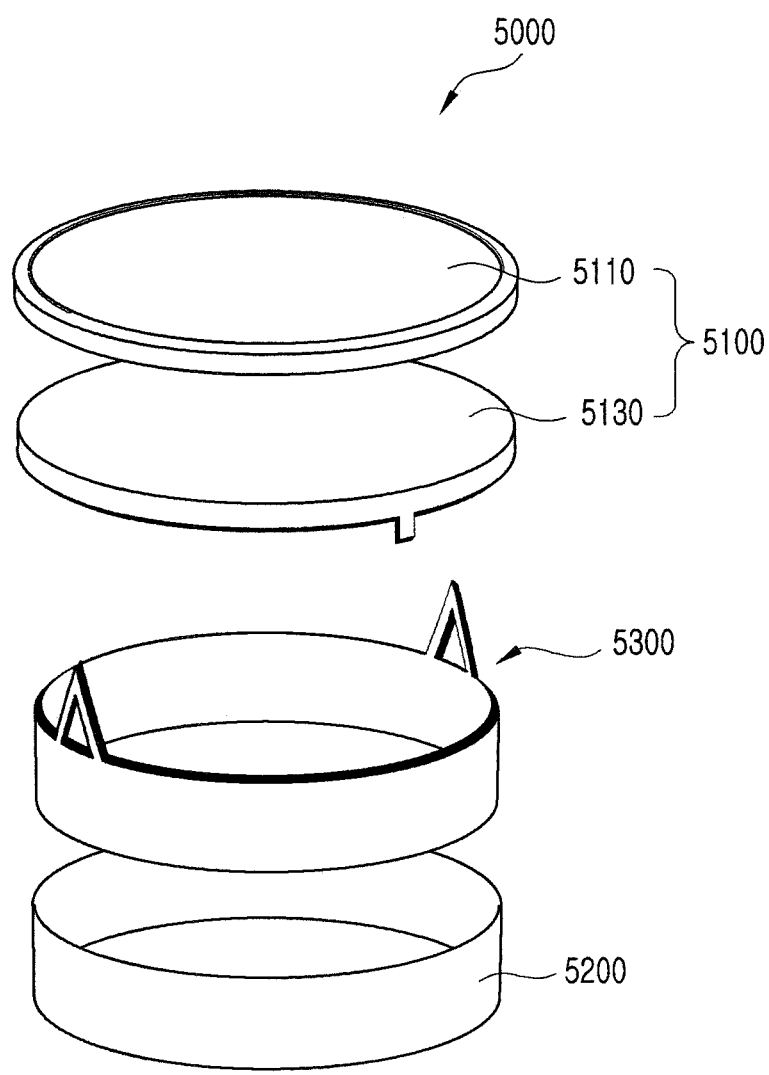
FIG. 13 is an exploded perspective view of the cell culture kit illustrated in FIG. 12.
Figure 14:
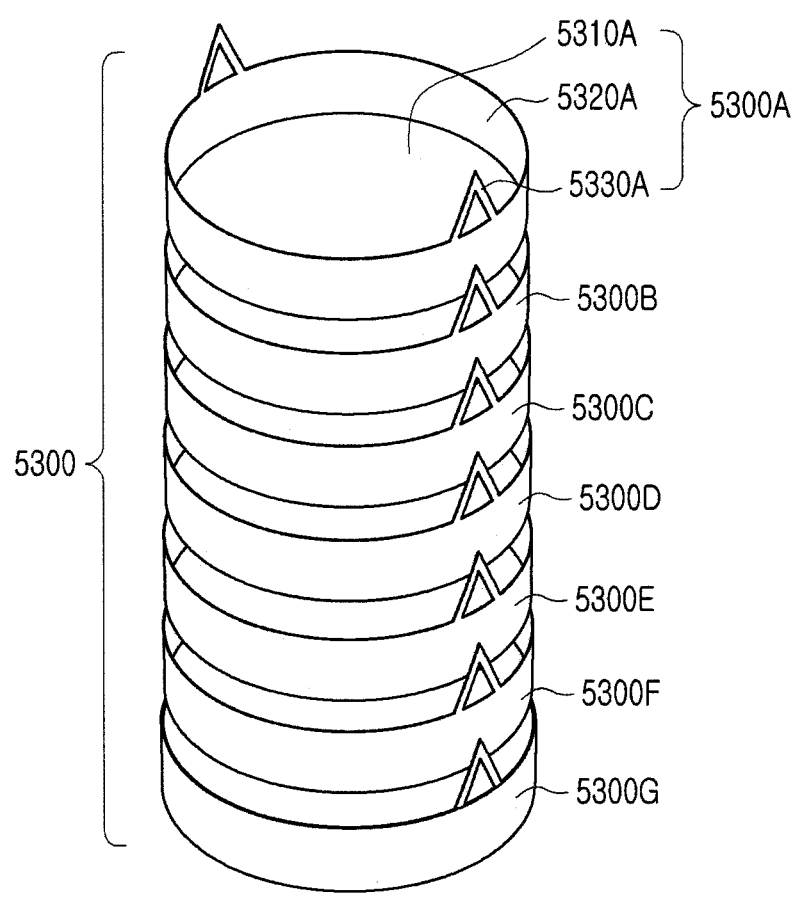
FIG. 14 is an exploded perspective view of the cell culture film illustrated in FIG. 13.
Figure 15:
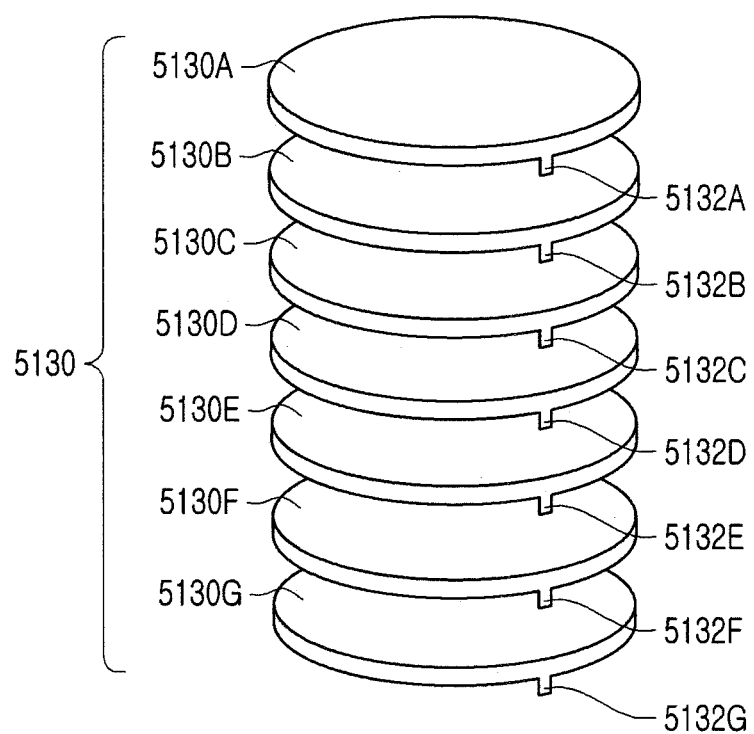
FIG. 15 is an exploded perspective view of an internal cover assembly illustrated in FIG. 13.

FIG. 12 is a perspective view of a cell culture kit 5000 according to another embodiment of the present invention. FIG. 13 is an exploded perspective view of the cell culture kit 5000. FIG. 14 is an exploded perspective view of a cell culture film assembly 5300 of FIG. 13. FIG. 15 is an exploded perspective view of an internal cover assembly 5130 included in a cover portion 5100 of FIG. 13.

Referring to FIGS. 12 to 15, the cell culture kit 5000 may include an external container 5200 configured with an open top to provide an accommodation space therein, cell culture films 5300A to 5300G formed by detachably stacking at least one piece inside the external container 5200, and the cover portion 5100 coupled to the open top of the external container 5200.

In this case, the cell culture films 5300A to 5300G may be configured in plural, to configure the cell culture film assembly 5300. The separate cell culture films 5300A to 5300G may each include a base 5310A with an upper surface on which a cell or a tissue is cultured and a side wall 5320A formed by bending an edge of the base 5310A upward.

In addition, a handle 5330A may be formed at an upper end portion of the side wall 5320A of the cell culture films 5300A to 5300G. The handle 5330A may extend upward from an upper end portion of the side wall of the cell culture films 5300A to 5300G. The handle 5330A may be formed in a triangular shape as illustrated or may be appropriately formed in a modified shape.

Accordingly, to separate the cell culture film 5300A at an uppermost end of the cell culture film assembly 5300, a handle 5330A of the cell culture film 5300A at the uppermost end may be pulled from the external container 5200 while being held to separate the cell culture film 5300A at the uppermost end.

As a result, the present embodiment is different from the aforementioned embodiments in that each of the cell culture films 5300A to 5300G according to the present embodiment includes the side wall 5320 extending upward as illustrated. As such, when each of the cell culture films 5300A to 5300G includes the side wall 5320, if a cell or a tissue is cultured on an upper surface of the base 5310 of the cell culture films 5300A to 5300G, an environment may be advantageously and easily conserved. That is, outward influences may be minimized compared with a case in which the side wall 5320 is not present.

As described above, when each of the cell culture films 5300A to 5300G includes the side wall 5320, the cover portion 5100 may include an external cover 5110 and the internal cover assembly 5130 including internal covers 5130A to 5130G detachably stacked inside the external cover 5110 to correspond to the number of the cell culture films 5300A to 5300G.

The internal cover assembly 5130 may be disposed inside the external cover 5110. In this case, the internal cover assembly 5130 may include the plural separate internal covers 5130A to 5130G and the number of the separate internal covers 5130A to 5130G may correspond to the number of the aforementioned separate cell culture films 5300A to 5300G.

That is, when the separate cell culture films 5300A to 5300G are separated, the separate internal covers 5130A to 5130G may be separated and coupled to side walls of the cell culture films 5300A to 5300G.

Accordingly, as such, when the cell culture films 5300A to 5300G include the side wall 5320 and include the separate internal covers 5130A to 5130G coupled to the side wall 5320, it may be advantageous to easily conserve an internal environment of the cell culture films 5300A to 5300G and to minimize outward influences.

In this case, the plural separate internal covers 5130A to 5130G may be detachably stacked. For example, the plural separate internal covers 5130A to 5130G may be heated to a predetermined temperature to be adhered to each other or may be adhered to each other using an adhesive formed of a material that does not affect growth of a cell or a tissue, such as resin or polymer resin of a silicone material.

In this case, the separate internal covers 5130A to 5130G may include separation handles 5132A to 5132G formed downward. Accordingly, to separate the internal covers 5130A to 5130G, the handle 5132G at a lowermost end among the internal covers 5130A to 5130G may be pulled from the external cover 5110 while being held to separate the internal cover 5130G at the lowermost end.

The internal covers 5130A to 5130G may be formed of a biocompatible material like the cell culture films 5300A to 5300G. For example, the internal covers 5130A to 5130G may be formed of polydimethylsiloxane (PDMS), poly (methylmethacrylate) (PMMA), a polystyrene film, or a silicone polymer.

Figure 16:
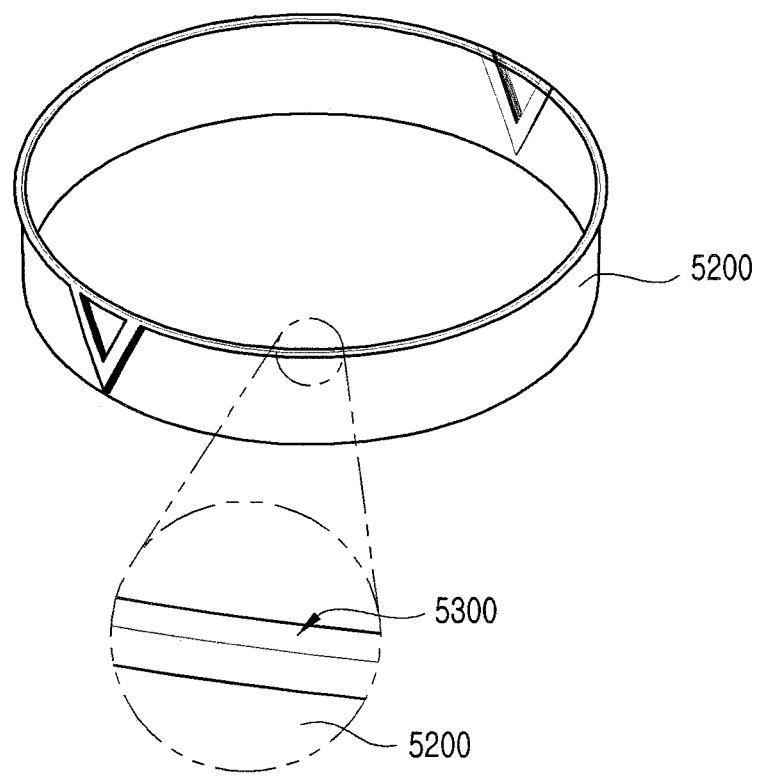
FIG. 16 is a perspective view showing a state in which an upper end portion of the cell culture film illustrated in FIG. 12 is folded upward.

FIG. 16 is a perspective view showing a state in which an upper end portion of the aforementioned the cell culture film assembly 5300 of FIG. 12 is folded outward.

Referring to FIG. 16, when the cell culture films 5300A to 5300G are stacked and positioned inside the external container 5200, a height of an upper end portion of a side wall of the cell culture film assembly 5300 may be higher than a height of an upper end portion of a side wall of the external container 5200.

In this case, when the upper end portion of the side wall of the cell culture film assembly 5300 is folded outward, the upper end portion of the side wall of the external container 5200 may be covered by the folded upper end portion of the cell culture film assembly 5300.

Accordingly, the cover portion 5100 may be easily coupled to an upper portion of the external container 5200.

The cell culture film assembly 5300 according to the present embodiment may include the plural separate cell culture films 5300A to 5300G and the separate cell culture films 5300A to 5300G may each include the side wall 5320.

In this case, when the side wall 5320 of each of the separate cell culture films 5300A to 5300G is perpendicularly formed, it may not be easy to stack the cell culture films 5300A to 5300G and may also not be easy to separate the separate cell culture films 5300A to 5300G.

Figure 17:
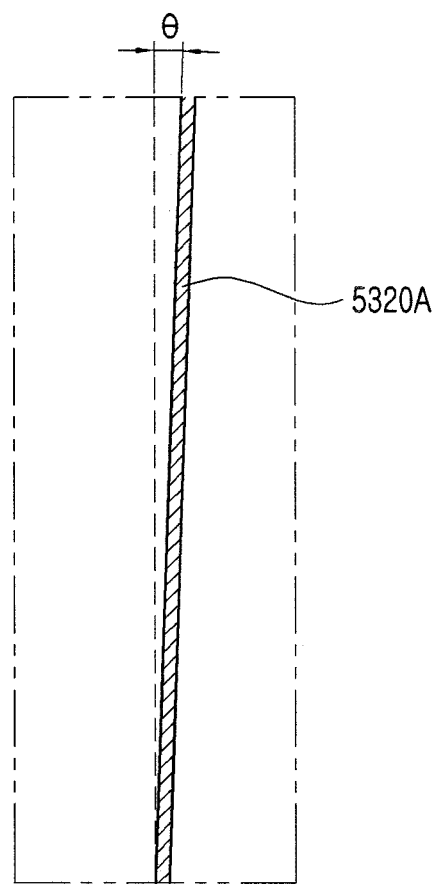
FIG. 17 is a lateral cross-sectional view of a side wall of a cell culture film.

Accordingly, as illustrated in FIG. 17, the side wall 5320 of each of the separate cell culture films 5300A to 5300G may be formed to be inclined outward at a predetermined angle based on a vertical line. FIG. 17 is a lateral cross-sectional view of a side wall 5320A of the cell culture film 5300A at a first layer.

Referring to FIG. 17, the side wall 5320A of the cell culture film 5300A at the first layer may be formed to be inclined outward at a predetermined angle θ, e.g., about 0.5° to about 1.5°, in detail, about 1° based on a vertical line.

As such, when the side wall 5320 of each of the separate cell culture films 5300A to 5300G is formed to be inclined outward, it may be easy to stack the separate cell culture films 5300A to 5300G. In addition, it may be easier to separate the separate cell culture films 5300A to 5300G.

Figure 18:
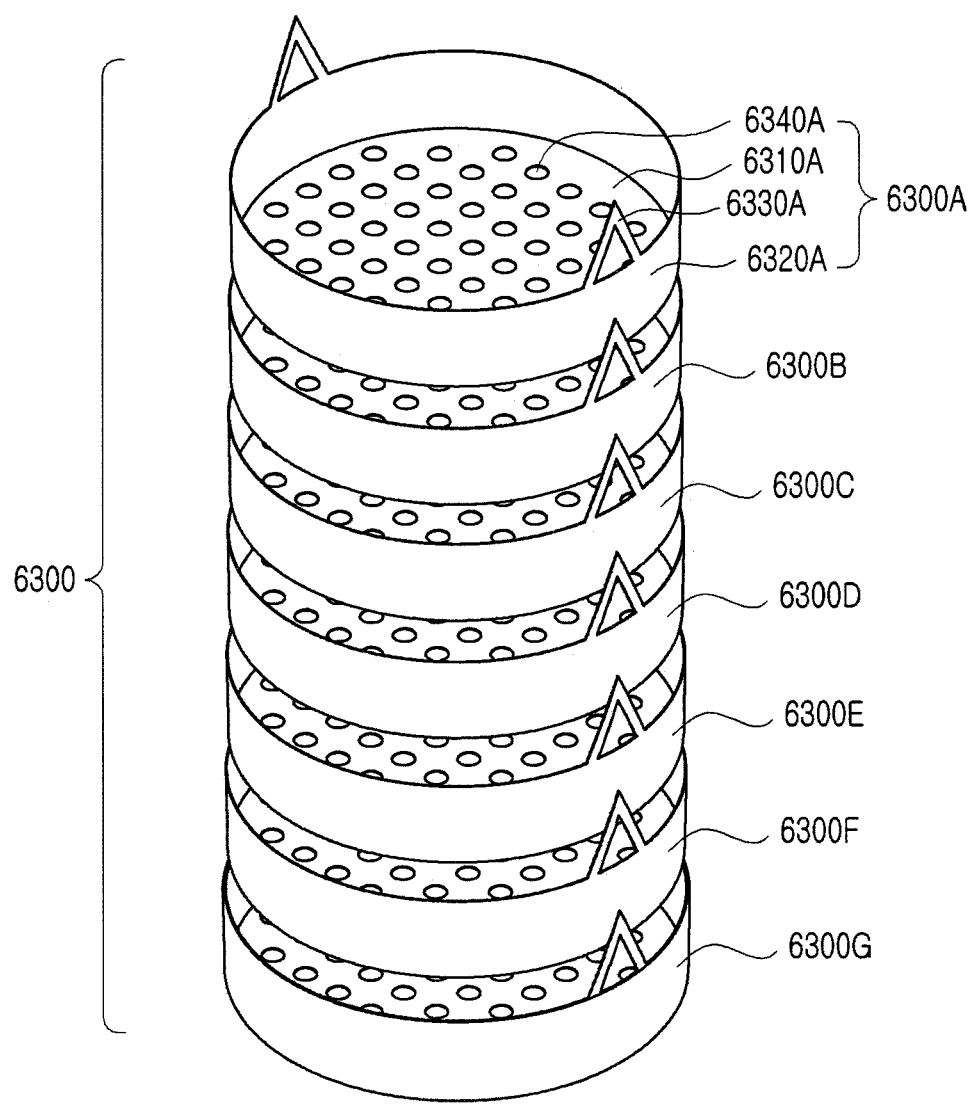
FIG. 18 is an exploded perspective view of a cell culture film according to another embodiment of the present invention.

FIG. 18 is an exploded perspective view of a cell culture film assembly 6300 according to another embodiment of the present invention.

The cell culture film assembly 6300 of FIG. 18 may be different from the aforementioned embodiments of FIGS. 12 and 14 in that a plurality of culture holes 6340A to 6340G are formed in cell culture films 6300A to 6300G, respectively.

In this case, the culture holes 6340A to 6340G of the cell culture films 6300A to 6300G may be formed not to overlap with culture holes of a cell culture film at a lower layer. A description of a base 6310, a side wall 6320, and a handle 6330 of the cell culture films 6300A to 6300G are similar to the above description of FIG. 14 and, thus, a repeated description is omitted. According to the present embodiment, the cell culture film assembly 6300 may include a plurality of internal covers (not shown) to be coupled to the separate cell culture films 6300A to 6300G.

When subculture is performed using the cell culture films 6300A to 6300G according to the present embodiment, trypsinization for separation of a cultured cell or tissue may be omitted, which is similar to the above description of FIGS. 10 and 11A-11D and, thus, a repeated description is omitted.

Figure 19:
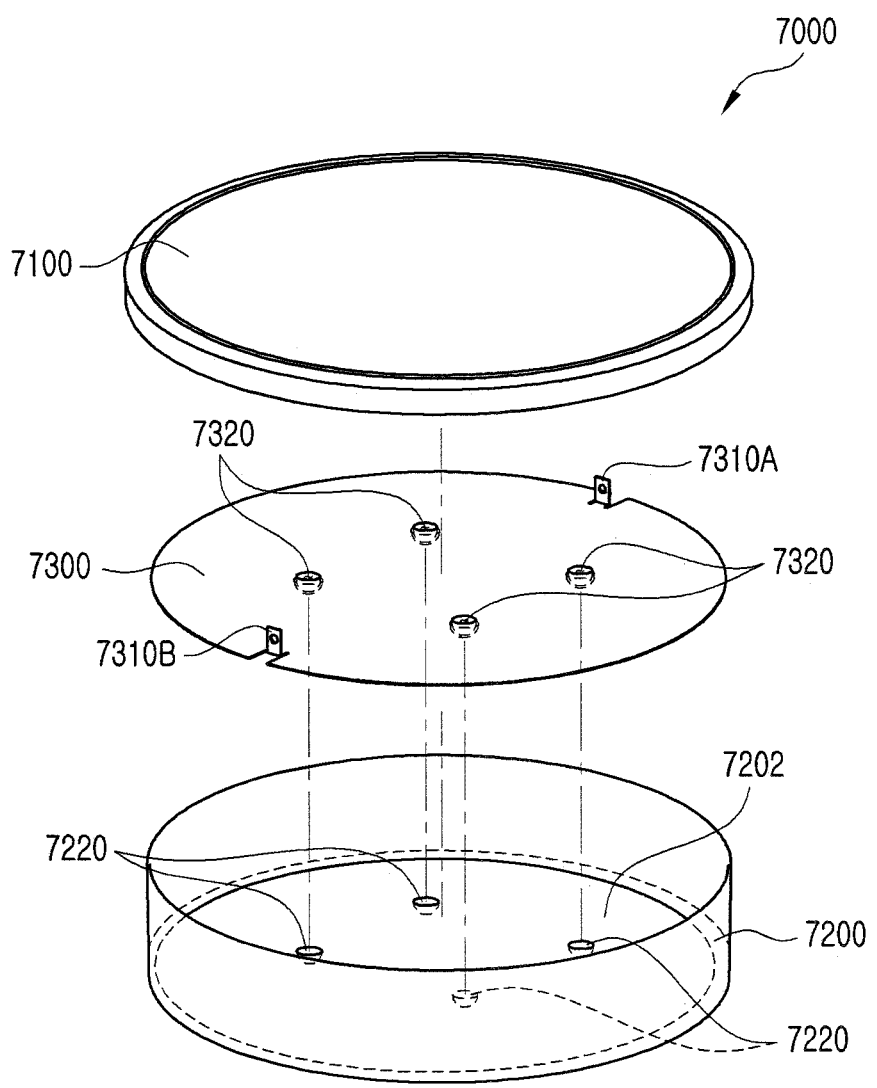
FIG. 19 is a perspective view of a cell culture kit for 3D cell culture according to another embodiment of the present invention.
Figure 20:
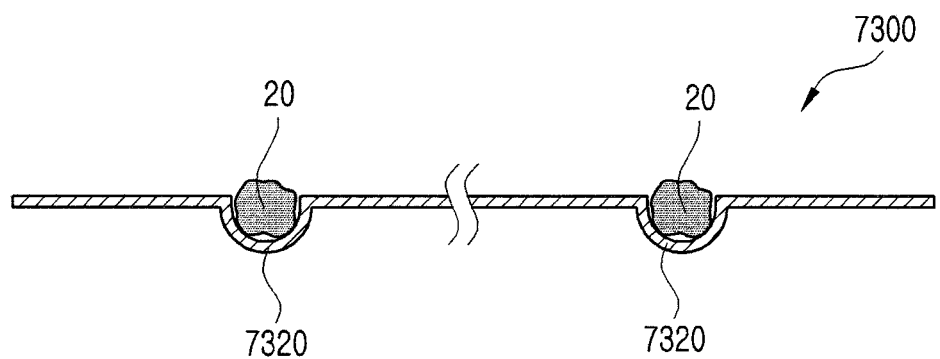
FIG. 20 is a lateral cross-sectional view of a cell culture film of FIG. 19.

FIG. 19 is a perspective view of a cell culture kit 7000 for 3D cell culture according to another embodiment of the present invention. FIG. 20 is a lateral cross-sectional view of a cell culture film 7300 of FIG. 19.

Referring to FIGS. 19 and 20, the cell culture kit 7000 according to the present embodiment may correspond to a cell culture kit to which 3D cell culture technology is applied. Recently, as research has been actively conducted into cells or stem cells of various organs, research has been conducted into a cell culture kit for culturing spheroids (hereinafter referred to as a cell assembly) that is a 3D assembly of a cell.

The cell culture kit 7000 illustrated in FIGS. 19 and 20 correspond to the cell culture kit 7000 for culturing such a cell assembly.

In detail, the cell culture kit 7000 may include an external container 7200 configured with an open top to provide an accommodation space therein, the cell culture film 7300 formed by detachably stacking at least one piece inside the external container 7200, and a cover portion 7100 coupled to the open top of the external container 7200.

In this case, the cell culture film 7300 may include at least one cell culture grooves 7320 protruding downward therein to culture a cell assembly 20 and, in this case, accommodation grooves 7220 for accommodation of the cell culture grooves 7320 therein may be formed in a base 7202 of the external container 7200 to correspond to the cell culture grooves 7320.

The cell culture film 7300 may include the cell culture grooves 7320 that protrude in a predetermined depth downward therein to culture the cell assembly 20. For example, the cell culture grooves 7320 may protrude toward a lower portion of the cell culture film 7300 to have a predetermined volume to 3-dimensionally culture the cell assembly 20 in the cell culture grooves 7320. In this case, the cell culture grooves 7320 are illustrated with a hemisphere shape in the drawing but are not limited thereto and, thus, the cell culture grooves 7320 may be modified in an appropriate form to culture the cell assembly 20 therein.

The cell culture grooves 7320 may protrude at a lower portion of the cell culture film 7300 and, thus, the accommodation grooves 7220 for accommodation of the cell culture grooves 7320 therein may be correspondingly formed in the base 7202 of the external container 7200.

The accommodation grooves 7220 may have an internal shape corresponding to a protruding shape of the cell culture grooves 7320 and the number of the accommodation grooves 7220 may correspond to the number of the cell culture grooves 7320.

In the case of the cell culture kit 7000 according to the present embodiment, the cell assembly 20 may be 3-dimensionally cultured in the cell culture grooves 7320 of the cell culture film 7300 and, then, a sample is prepared via frozen sectioning and may be observed or examined using a microscope.

In this case, the cell culture film 7300 may function as a mould without a separate mould to conveniently and simply prepare a sample and, thus, it may be possible to observe a cell assembly.

The cell culture film 7300 may have a thickness of about 0.1 mm to about 0.2 mm and may be manufactured with a refractive index corresponding to about 1.4 to about 1.6.

In addition, the cell culture film 7300 may be formed of a transparent biocompatible material. For example, the cell culture film 7300 may be formed of polydimethylsiloxane (PDMS), poly(methylmethacrylate) (PMMA), a polystyrene film, or a silicone polymer.

The cell culture film 7300 may include a pair of handle portions 7310A and 7310B along an edge of the cell culture film 7300 to be easily separated from the external container 7200.

The cell culture film 7300 may be detachably positioned on an upper surface of the base 7202 of the external container 7200.

For example, the cell culture film 730 may be heated to a predetermined temperature to be adhered to the base 7202 of the external container 7200 or the cell culture film 730 and the base 7202 may be adhered using an adhesive formed of a material that does not affect growth of a cell or a tissue, such as resin or polymer resin of a silicone material.

The cover portion 7100 has been described above and, thus, a repeated description is omitted herein.

Figure 21:
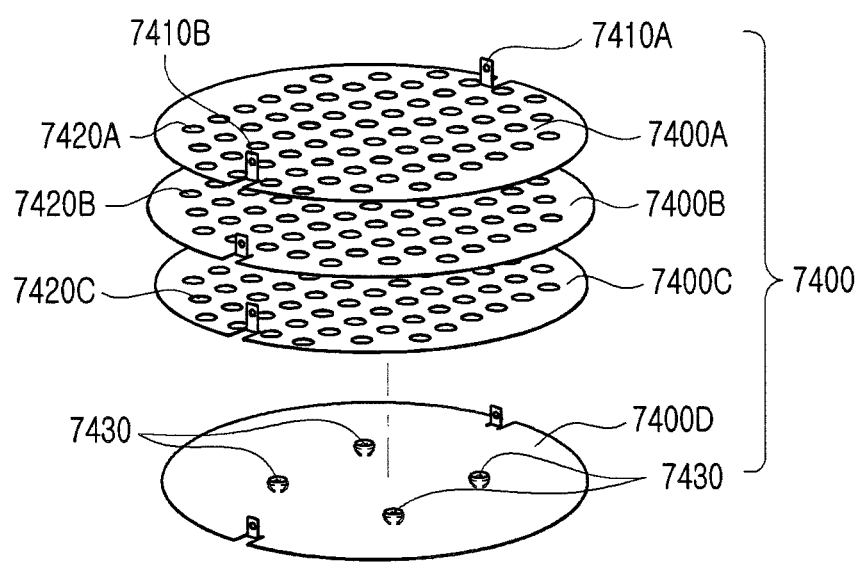
FIG. 21 is an exploded perspective view of a cell culture film according to another embodiment of the present invention.

FIG. 21 is an exploded perspective view of a cell culture film according to another embodiment of the present invention.

Referring to FIG. 21, cell culture films 7400A, 7400B, 7400C, and 7400D may be configured in plural to configure a cell culture film assembly 7400.

In this case, the cell culture film 7400D formed with the aforementioned cell culture groove 7430 therein may be positioned at a lowermost layer of the cell culture film assembly 7400 and at least one of the cell culture films 7400A, 7400B, and 7400C with a plurality of culture holes 7420A, 7420B, and 7420C formed therein may be positioned above the cell culture film 7400D at the lowermost layer.

That is, the cell culture film 7400D with the cell culture groove 7430 formed therein may be disposed at the lowermost layer of the cell culture film assembly 7400 and the cell culture films 7400A, 7400B, and 7400C with the plural culture holes 7420A, 7420B, and 7420C formed therein may be disposed above the cell culture film 7400D.

In this case, a structure formed by detachably stacking the cell culture films 7400A, 7400B, 7400C, and 7400D has been already described above and, thus, a repeated description is omitted herein.

At least one culture holes 7420A', 7420B', and 7420C' (refer to FIGS. 22A to 22D) of the culture holes 7420A, 7420B, and 7420C in the cell culture films 7400A, 7400B, and 7400C may be disposed to be connected to the cell culture groove 7430 in the cell culture film assembly 7400 having the aforementioned structure. In this case, the remaining culture holes of the cell culture films 7400A, 7400B, and 7400C may not overlap with culture holes of cell culture films at a lower layer.

FIGS. 22A to 22D are lateral cross-sectional views of the cell culture film assembly 7400 illustrated in FIG. 21 and shows subculture and a procedure of growing a 3D cell assembly using the cell culture film assembly 7400 illustrated in FIG. 21.

Figure 22A:
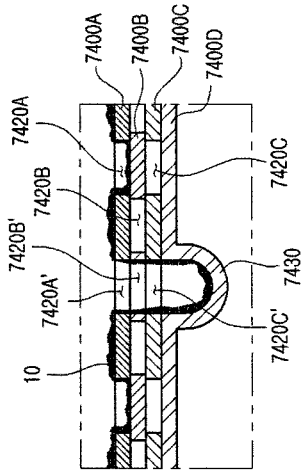
FIGS. 22A to 22D show subculture and a procedure of growing a 3D cell assembly using the cell culture film assembly illustrated in FIG. 21.

Referring to FIG. 22A, the cell culture film 7400D with the cell culture groove 7430 formed therein may be disposed at a lowermost layer of the cell culture film assembly 7400 and the cell culture films 7400A, 7400B, and 7400C with the plural culture holes 7420A, 7420B, and 7420C formed therein may be positioned above the cell culture film 7400D.

In this case, at least one culture holes 7420A', 7420B', and 7420C' of the plural culture holes 7420A, 7420B, and 7420C with the cell culture films 7400A, 7400B, and 7400C formed therein respectively may be disposed to be connected to the cell culture groove 7430. That is, at least one 7420A', 7420B', and 7420C' may be arranged to overlap with each other.

In this case, the remaining culture holes 7420A, 7420B, and 7420C of the cell culture films 7400A, 7400B, and 7400C may not overlap with culture holes of a cell culture film at a lower layer.

In this case, as illustrated in FIG. 22A, a tunnel may be formed in a perpendicular direction toward the cell culture groove 7430 of the cell culture film 7400D at a lowermost layer from the cell culture film 7400A at an uppermost layer through the culture holes 7420A', 7420B', and 7420C' connected to the cell culture groove 7430.

When such a structure is configured, subculture is performed and, simultaneously, a 3D cell assembly may be grown and, thus, this will be described below with reference to FIGS. 22A to 22D.

First, referring to FIG. 22A, the cell or tissue 10 may be cultured on an upper surface of the cell culture film 7400A at a first layer of the cell culture film assembly 7400.

Figure 22B:
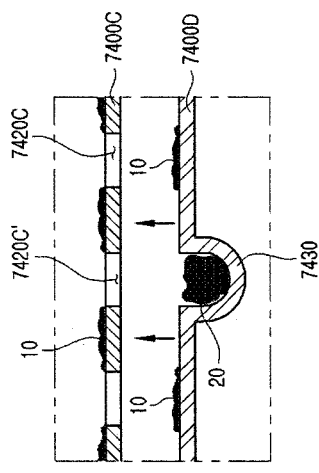

In this case, the cultured cell or tissue 10 may be cultured to cover the upper surface of the cell culture film 7400A at the first layer and, then, as illustrated in FIG. 22B, may also be cultured on an upper surface of the cell culture film 7400B at the second layer, which is exposed through the culture holes 7420A.

The cultured cell or tissue 10 may be grown upward to the cell culture groove 7430 at a lower layer through the culture holes 7420A', 7420B', and 7420C' connected to each other.

That is, a tunnel is formed in a perpendicular direction to the cell culture groove 7430 through the culture holes 7420A', 7420B', and 7420C' connected to each other and, thus, as a cell or a tissue is grown downward to the cell culture groove 7430 through the tunnel to be 3-dimensionally grown in an internal space of the cell culture groove 7430.

Figure 22C:
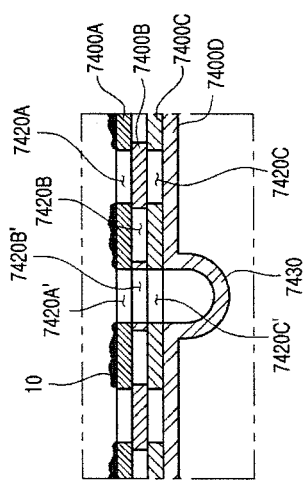

In this case, when an operator pulls handle portions 7410A and 7410B (refer to FIG. 21) of the cell culture film 7400A at the first layer to separate the cell culture film 7400A at the first layer from the cell culture film 7400B at the second layer as shown in FIG. 22C, the cultured cell or tissue may remain on a portion of an upper surface of the cell culture film 7400B at the second layer as well as an upper surface of the cell culture film 7400A at the first layer.

Accordingly, a cell or a tissue may be continuously cultured on the upper surface of the cell culture film 7400B at the second layer and, thus, separate trypsinization for separating the cell or the tissue for subculture may not be required unlike in the prior art.

In this case, the cell or the tissue may be cultured in the cell culture groove 7430 to have a shape of the cell assembly 20.

The cell assembly 20 has a 3D shape and, thus, may be grown for longer time than a cell or a tissue that is 2-dimensionally grown on an upper surface of the cell culture films 7400A, 7400B, and 7400C.

Figure 22D:
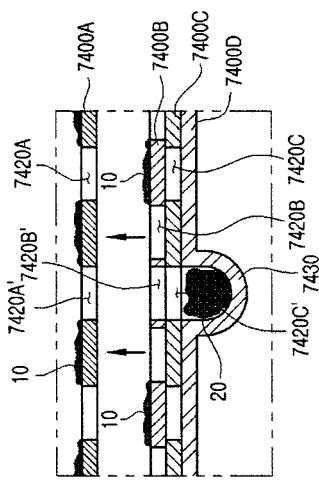

Accordingly, a cell or a tissue may be observed and examined via subculture while sequentially separating the cell culture films 7400A, 7400B, and 7400C with the culture holes 7420A, 7420B, and 7420C respectively formed therein and, in this case, may be continuously grown in the cell culture grooves 7430 to have a shape of the cell assembly 20 to examine and observe the 3D cell assembly 20 as shown in FIG. 22D.

A cell culture kit according to the present invention may include a plurality of stacked cell culture films and, thus, a tissue or a cell may be cultured on an upper surface of a base of the cell culture film and, then, the cell culture film may be separated and observed without change.

Accordingly, a procedure of separating a cultured cell or tissue from a culture dish to move the cell or the tissue to a cover glass for biopsy may be omitted. Accordingly, it may not be required to inject an external cover glass into a cell culture container and, thus, an engraftment rate of a cell may not be changed, thereby preventing change in a cell culture environment.

In addition, cell or tissue metamorphosis during movement of the cultured cell or tissue may be prevented and the cell or the tissue may be easily and rapidly examined.

When a cell culture kit according to the present invention requires subculture, separate trypsinization may not be required to separate a cell and, accordingly, cell or tissue metamorphosis during trypsinization may be prevented.

According to the present invention, a cell or a tissue may be 2-dimensionally grown and, simultaneously, a 3D cell assembly may be grown therewith and, thus, it may be possible to observe and examine the cell assembly along with general examination of a grown cell.

The foregoing exemplary embodiments and advantages are merely exemplary and are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A cell culture kit comprising:
an external container having an open top and a closed base to provide an accommodation space therein;
at least one cell culture film detachably stacked inside the external container; and
a cover portion coupled to the open top of the external container,
wherein the at least one cell culture film includes:
a first film disposed within the external container; and
a second film disposed between the first film and the base of the external container, the second film detachably adhering to the first film,
wherein the first film includes:
a first top surface on which a cell is cultured;
a first bottom surface facing the second film; and
a plurality of first culture holes formed at a body of the first film, the plurality of first culture holes passing through the first top and bottom surfaces of the first film,
wherein the second film includes:
second top and bottom surfaces facing the first bottom surface of the first film and the base of the external container, respectively; and
a plurality of second culture holes formed at a body of the second film, the plurality of second culture holes passing through the second top and bottom surfaces of the second film,
wherein the second top surface of the second film contacts the first bottom surface of the first film and the plurality of first culture holes do not overlap with the plurality of second culture holes, such that the cell on the first top surface is transferred and cultured on the second top surface which is exposed via the plurality of the first culture holes,
wherein the second film further includes a culture groove formed at a body of the second film and protruding downwardly toward the base of the external container, the culture groove having an open top and a closed bottom to form an inner space and accommodating a cell assembly in the inner space to be cultured,
wherein the at least one cell culture film includes a tunnel formed from the first top surface of the first film to the inner space of the culture groove of the second film.

2. The cell culture kit of claim 1, wherein the at least one cell culture film is formed of a polystyrene film or a silicone polymer.

3. The cell culture kit of claim 1, wherein the at least one cell culture film has a thickness of 0.1 to 0.2 mm.

4. The cell culture kit of claim 1, wherein the at least one cell culture film has a refractive index corresponding to 1.4 to 1.6.

5. The cell culture kit of claim 1, further comprising a handle portion extending upward from an edge of the at least one cell culture film, the handle portion comprising a portion of the at least one cell culture film.

6. The cell culture kit of claim 1, further comprising a side wall bent upward from an edge of the at least one cell culture film, the side wall being configured to enclose the cell cultured on the top surface of the at least one cell culture film.

7. The cell culture kit of claim 6, wherein the side wall of the at least one cell culture film is formed to be inclined outward at a predetermined angle based on a vertical line.

8. The cell culture kit of claim 6, further comprising a handle disposed at an upper end portion of the side wall of the at least one cell culture film.

9. The cell culture kit of claim 6, wherein a height of an upper end portion of the side wall of the at least one cell culture film is greater than a height of an upper end portion of a side wall of the external container.

10. The cell culture kit of claim 9, wherein, when the upper end portion of the side wall of the at least one cell culture film is folded outward, the upper end portion of the side wall of the external container is covered by the folded upper end portion of the at least one cell culture film.

11. The cell culture kit of claim 6, wherein the cover portion comprises an external cover and an internal cover that is stacked inside the external cover, wherein the internal cover is configured to be detached from the external cover to cover the at least one cell culture film which is detached from the external container.

12. The cell culture kit of claim 11, wherein the internal cover further includes a handle to be gripped when the internal cover is detached from the external cover.

13. The cell culture kit of claim 1, wherein the external container includes an accommodation groove formed at the base of the external container and receiving the closed bottom of the culture groove.

14. The cell culture kit of claim 1, wherein the tunnel comprises:

a through hole formed at the first film and configured to directly communicate with the culture groove of the second film; and the open top of culture groove aligned in a vertical direction with the through hole to allow the cell on the first top surface of the first film to move directly into the inner space of the culture groove via the tunnel.

* * * * *